United States Patent [19]

DeWall

[11] 3,994,689
[45] Nov. 30, 1976

[54] METABOLIC BUBBLE OXYGENATOR

[76] Inventor: Richard A. DeWall, 247 Northview Road, Dayton, Ohio 45419

[22] Filed: Oct. 31, 1973

[21] Appl. No.: 411,332

Related U.S. Application Data

[63] Continuation of Ser. No. 178,647, Sept. 8, 1971, abandoned.

[52] U.S. Cl. .................. 23/258.5 B; 128/DIG. 3; 195/1.8; 261/DIG. 28
[51] Int. Cl.² .......................................... A61M 1/03
[58] Field of Search ................... 23/258.5; 195/1.8; 261/DIG. 28; 128/DIG. 3

[56] References Cited
UNITED STATES PATENTS

| | | | |
|---|---|---|---|
| 2,854,002 | 9/1958 | DeWall et al. | 23/258.5 |
| 2,934,067 | 4/1960 | Calvin | 23/258.5 |
| 3,052,238 | 9/1962 | Broman et al. | 128/DIG. 3 |
| 3,058,464 | 10/1962 | Broman | 23/258.5 |
| 3,087,490 | 4/1963 | Broman | 23/258.5 |
| 3,112,746 | 12/1963 | Gewecke et al. | 23/258.5 |
| 3,175,555 | 3/1965 | Ling | 23/258.5 |
| 3,502,440 | 3/1970 | Tompkins | 23/258.5 |
| 3,513,845 | 5/1970 | Chesnut et al. | 23/258.5 X |
| 3,526,481 | 9/1970 | Rubricius | 23/258.5 |
| 3,527,572 | 9/1970 | Urkiewicz | 23/258.5 |
| 3,536,451 | 10/1970 | Ludwin | 23/258.5 |
| 3,565,405 | 2/1971 | Black | 261/124 X |
| 3,729,377 | 4/1973 | Leonard | 23/258.5 X |
| R27,100 | 3/1971 | DeWall | 23/258.5 |

Primary Examiner—Morris O. Wolk
Assistant Examiner—Michael S. Marcus
Attorney, Agent, or Firm—Hofgren, Wegner, Allen, Stellman & McCord

[57] ABSTRACT

A bubble oxygenator having a generally cubic exterior housing with a gas dispersion system having a one-way valve that prevents the backflow of blood into the oxygen supply. At one end of the oxygenator housing is a generally vertically extending bubble chamber having a movable wall to vary the flow capacity of the oxygenator. Formed separately from the bubble or oxygenating chamber is a generally horizontally extending bubble collection chamber in the top of the cubic housing. The bubble collection chamber is formed by a rectangular envelope shaped, defoaming mesh and filter assembly. A planar temperature controlled ramp receives debubbled blood from the bubble collection chamber and directs it in planar fashion downwardly toward a reservoir.

10 Claims, 13 Drawing Figures

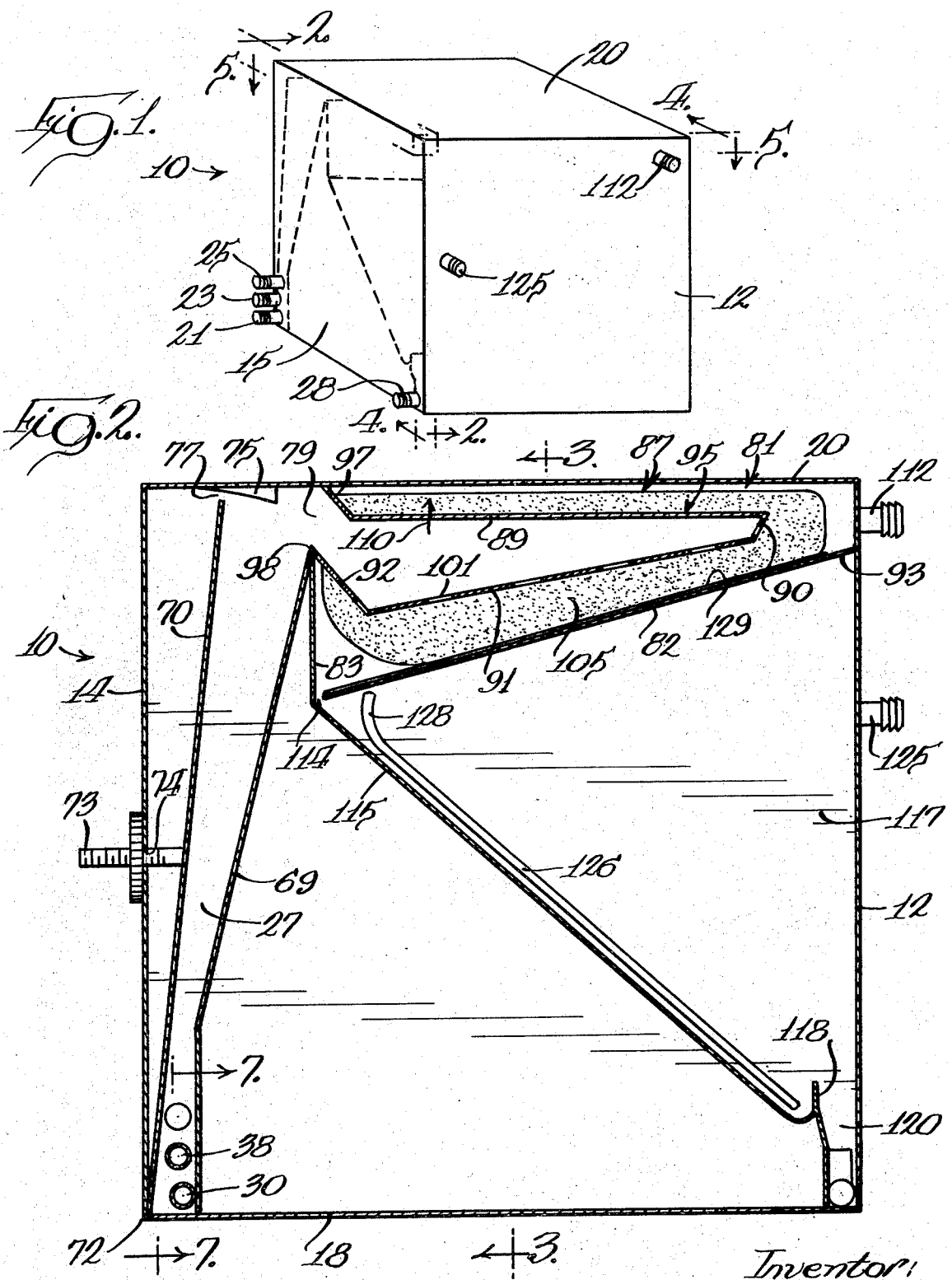

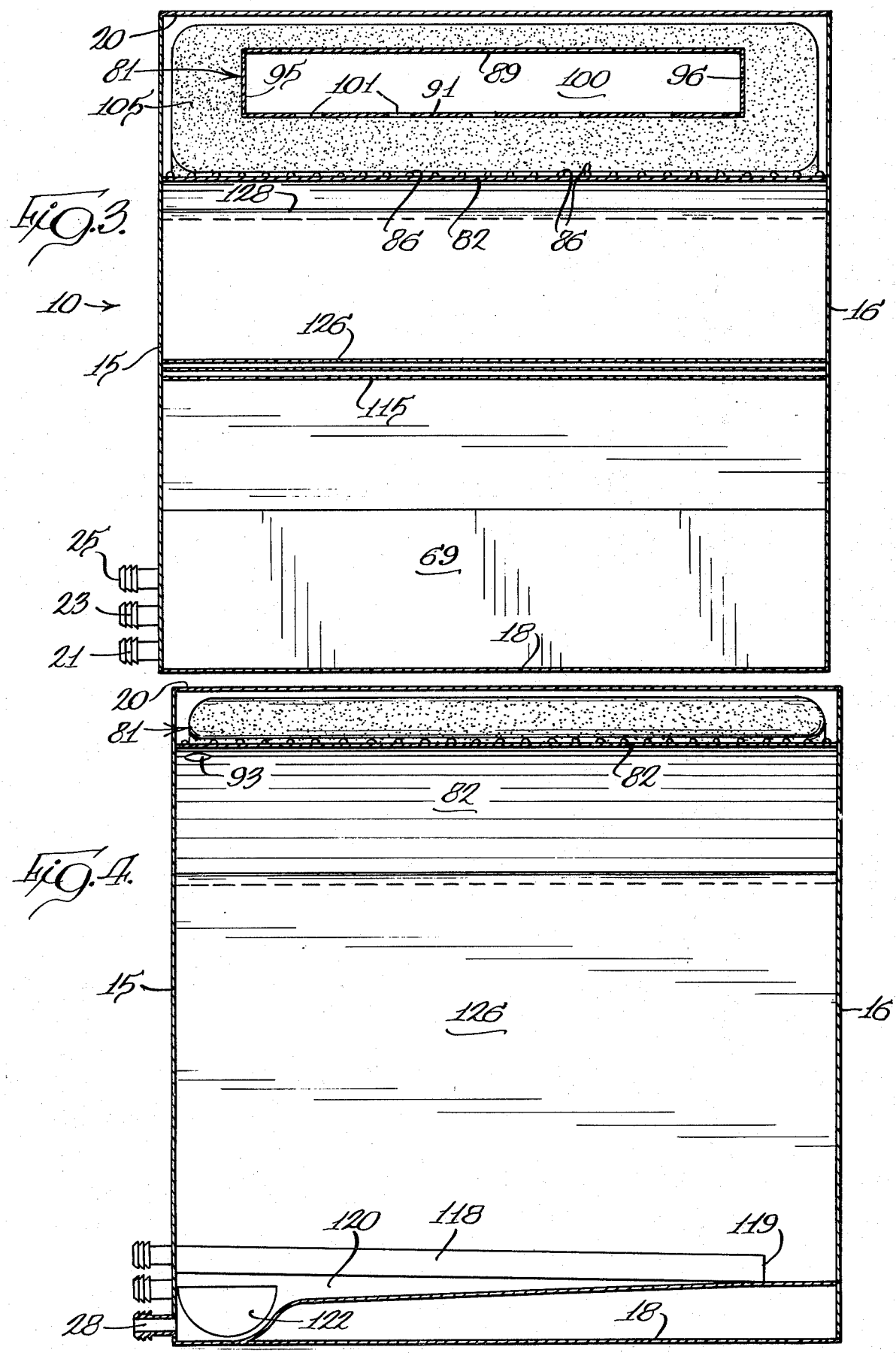

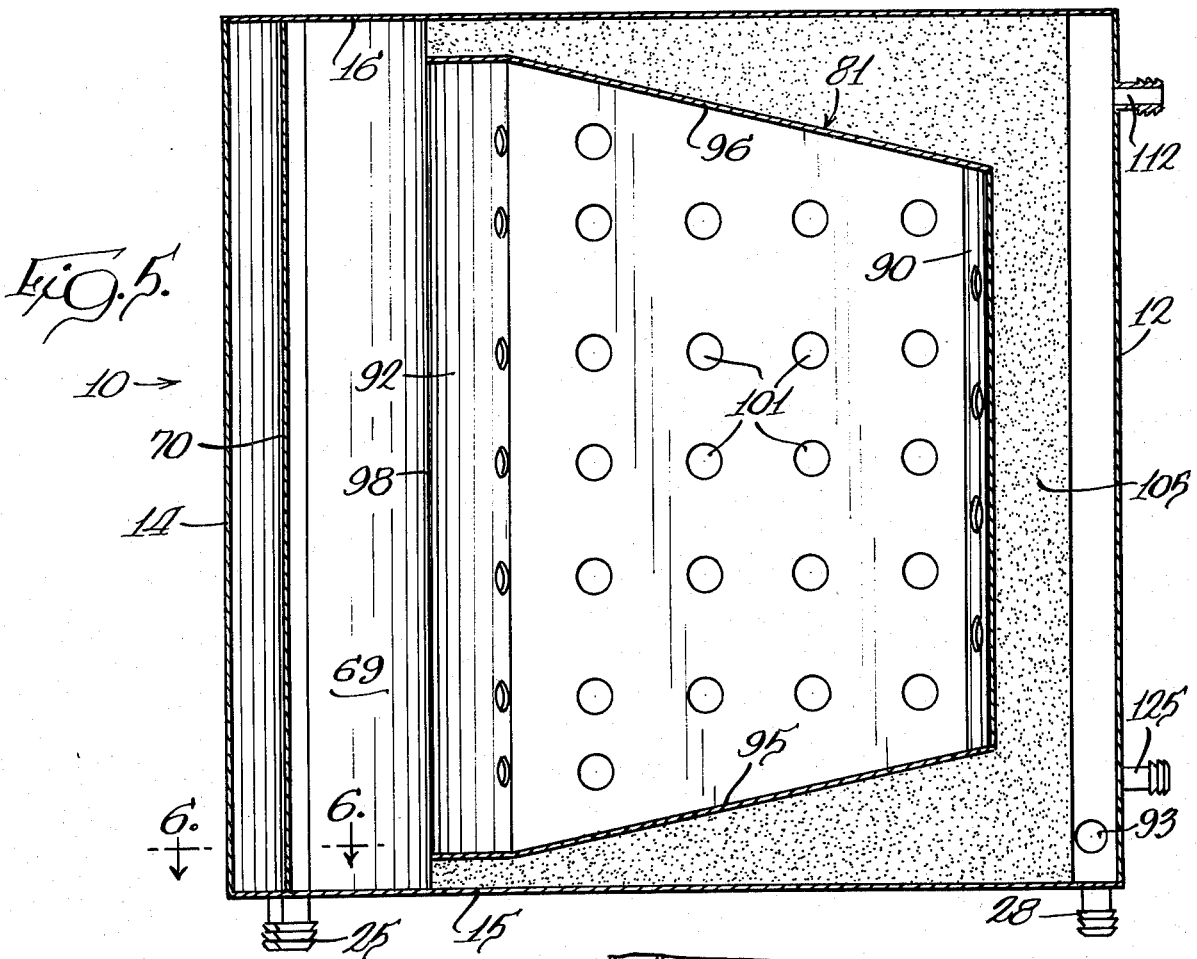
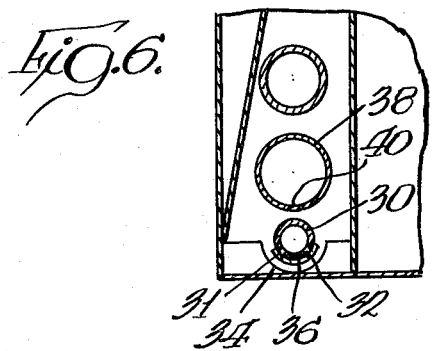
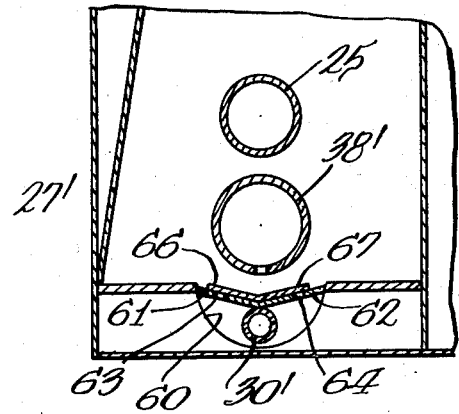
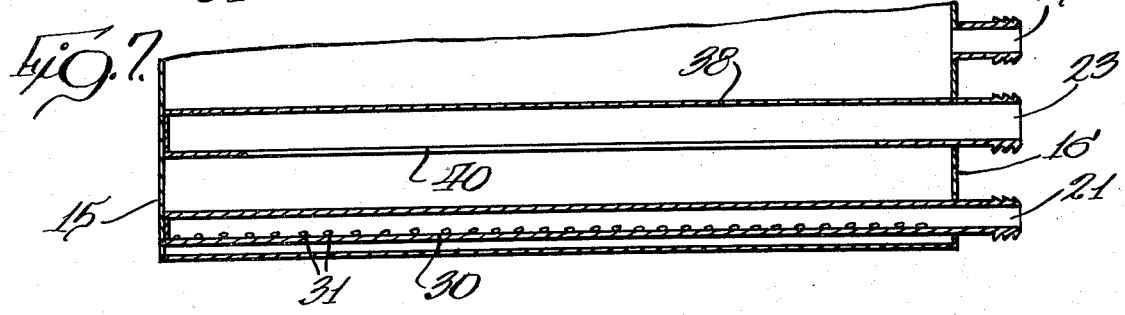

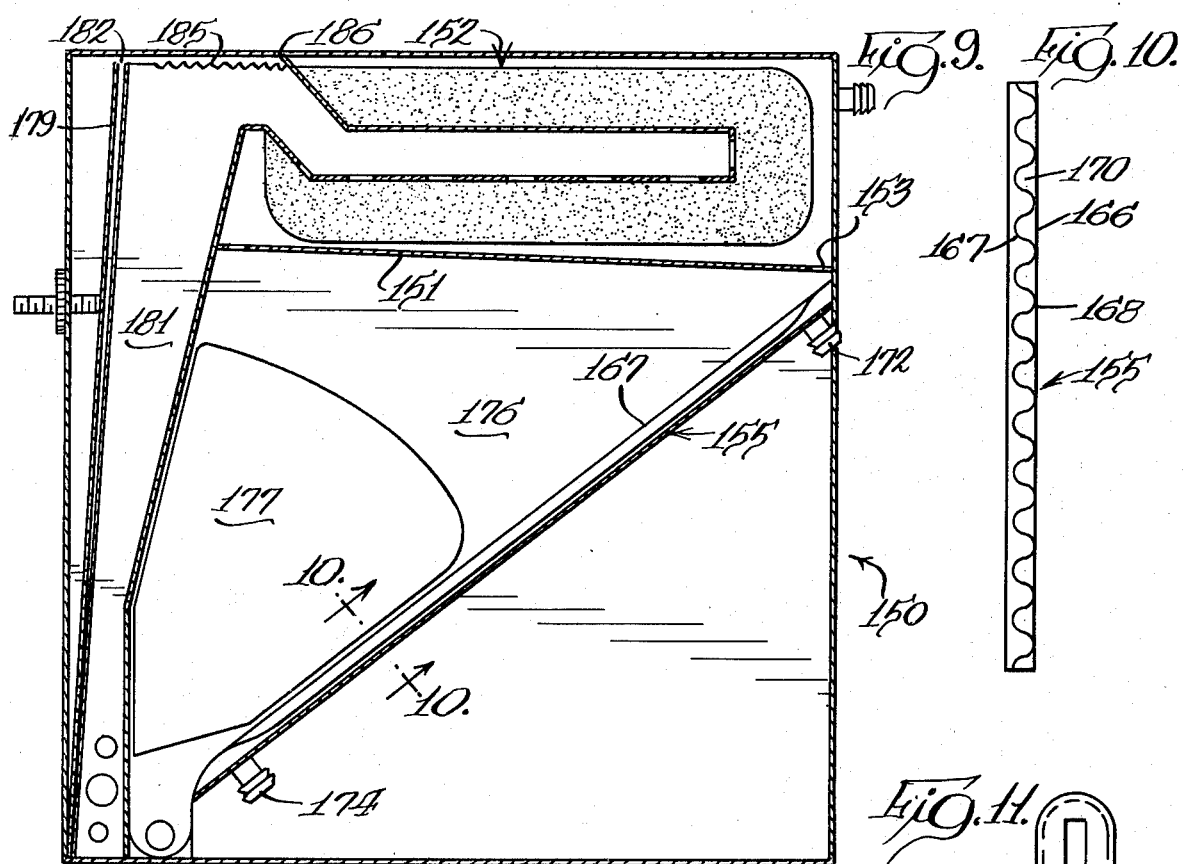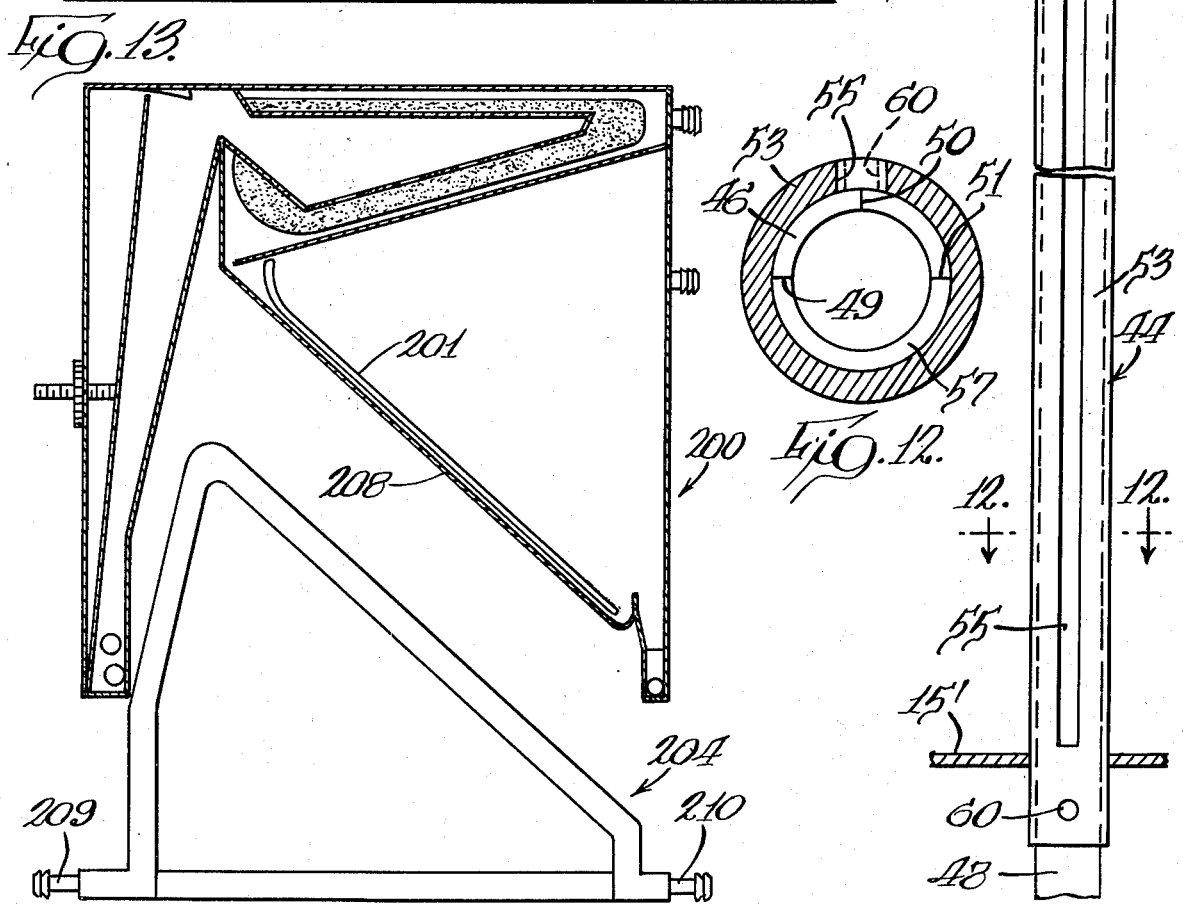

METABOLIC BUBBLE OXYGENATOR

This application is a streamline continuation of patent application Ser. No. 178,647 filed September 8, 1971, now abandoned.

BACKGROUND OF THE PRESENT INVENTION

There are three types of oxygenators in prevalent use today; the bubble oxygenator, the surface filming oxygenator and the membrane oxygenator. Artificial oxygenators have been highly successful in providing the human respiratory function in a cardiopulmonary bypass employed, for example, during open-heart surgery. The present invention relates primarily to oxygenators of the bubble type, though certain features thereof may be applicable to one of the other types of oxygenators.

There are a plurality of variables relevant to respiratory gas dispersion into venous blood which are considered in the design of the primary features of the present invention. It is believed helpful to identify these variables and evaluate their effect with respect to the blood oxygenating and carbon dioxide release process of the pulmonary function.

The first of these variables is the blood flow rate into the gas exchange system. The blood flow rate into an extracorporeal respiratory gas and blood exchange system is primarily at rates less than 7 liters per minute, although the rate varies from one patient to another and, in fact, varies in the same patient depending upon other physiological conditions.

A second variable is the respiratory gas mixture, i.e. the percentage of oxygen and carbon dioxide flowing into the system. A mixture of 98% oxygen and 2% carbon dioxide is often used, however, other mixtures can be used depending upon other variables in the system. The appropriate ratio is determined by sampling the patient's blood and measuring the gas content of the blood after processing so that if excessive or insufficient amounts of carbon dioxide are removed from the blood, this can be adjusted.

The respiratory gas flow rate is another variable and is often in the range of 1 to 5 parts of respiratory gas to 1 part of blood for the process. If the blood is excessively or insufficiently saturated with oxygen, adjustments are made in the quantity of respiratory gas mixture introduced into the oxygenator.

Still another variable is the time period during which blood and oxygenating gas are exposed to one another. The longer the time of contact, the more absolute the maximum exchange of blood with the gas. Gas exchange may be defined as the release of excess of carbon dioxide from the blood and the addition of sufficient oxygen to the blood to change it from a venous to an arterial state. Moreover, carbon dioxide is 20 times more soluble in blood than oxygen so that the longer the time of blood-gas contact, the greater will be the saturation of the blood with carbon dioxide.

A further variable is the thickness of the film of blood around each aliquot of respiratory gas. Efficiency or rate of blood-gas equilibration in an extracorporeal blood respiratory gas exchange system is highly dependent upon the thickness of the blood around each aliquot of respiratory gas. For example, a liter of venous blood with a few marble sized bubbles of gas will have a very thick blood cell between the gas bubbles. Therefore, a great amount of time would be necessary for the gas of these few bubbles to penetrate the diffusion gradients of the blood and equilibrate. The greater the number of bubbles for a given volume of blood, the less the distance that the gas must penetrate to equilibrate.

The relative diameter of each blood bubble is important to the exchange process in the following manner. By progressively making smaller bubbles with a given aliquot of gas, the surface of exposure of the blood to the gas phase is markedly increased. Moreover, as more smaller bubbles are introduced into the system for a given volume of blood, the thickness of the blood between the bubbles decreases and the rate of respiratory exchange increases as the diffusion distance for the gas through the blood has progressively diminished.

As the bubbles become extremely small, the ratio of the surface of that bubble to its volume becomes very large. As the surface of the tiny bubble represents a finite quantity of blood, containing respiratory gases, the gases will rapidly equilibrate between the blood and the gas within the bubble. As mentioned, carbon dioxide is greater than 20 times more soluble in the blood than oxygen. As the available volume of the bubble is small compared to the surface film, the partial pressures of gas stabilizes with the extraction of an insufficient amount of the carbon dioxide. As oxygen is absorbed from the bubble into the blood, the volume of the bubble decreases to the extent of the lost oxygen, and increases to the extent of the released carbon dioxide. But the percentage of carbon dioxide in the respiratory gas is about only 2%. Therefore, extremely small bubbles tend to retain carbon dioxide in excess of the demand and therefore there is an ultimate and optimum bubble size generally avoiding microbubbles.

One of the objects of the present invention is to provide an oxygenator that optimizes bubble size to effect the most efficient blood-gas exchange.

According to the LaPlace equation ($T=kPR$), the tension on the wall of a plastic (or non-rigid) sphere is in direct proportion to the pressure in the sphere and its diameter. Therefore, a bubble with a constant pressure develops an increasing tension on its walls as its diameter increases. IF the diameter is made to increase excessively, the tension produced by the surface tension of the fluid content of the blood and its own elasticity increases to a point that it cannot maintain its integrity and the bubble ruptures. Therefore, larger bubbles are easier to remove from the system than smaller bubbles as the larger bubbles tend to destroy themselves.

Thus, it may be determined to have smaller optimum bubbles at the point of oxygenation within the oxygenator and larger bubbles that may be easily ruptured at the point in the system where bubble collection and defoaming occur. The initial diameter of the bubble is influenced by the size of the aperture and rate of the introduction of respiratory gas into the blood. Also, a bubble rising in a column of blood (and bubbles) increases in size due to the decreasing hydrostatic pressure.

The temperature of the blood influence the reaction between the blood and the respiratory gases. As the temperature decreases from normal, the blood will be saturated at progressively lower partial pressures of the oxygen. The tissues require less oxygen for the metabolic function as temperature decreases. If saturated cold blood is supplied with a lower partial pressure $pO_2$, the pressure differential between the blood and the tissues is minimized and the oxygen becomes less available to the tissues. Warm blood supplied in a saturated condition has a much higher partial pressure $pO_2$, and, therefore, a greater partial pressure difference between the tissues and the blood, and a greater tendency for the flow of oxygen from the blood to the tissues. For these reasons, an efficient temperature control system is highly desirable in an oxygenator.

It is a primary object of the present invention, with these variables in consideration, to provide a bubble oxygenator having optimum bubble size, gas diffusion, debubbling and defoaming, and planar flow temperature control of the blood.

SUMMARY OF THE PRESENT INVENTION

According to the present invention, a generally cubic bubble oxygenator is provided. Throughout the oxygenator generally planar flow channels are provided to (1) increase the even distribution of gas bubbles within the oxygenating chamber (2) increase the efficiency of the defoaming process in a bubble collection chamber separate from the oxygenating chamber, and (3) provide laminar flow over a heating ramp increasing the heating uniformity of the blood.

In one embodiment, a gas dispersion system is provided in the bottom of the oxygenating chamber including a horizontally extending gas dispersion tube. This tube has a plurality of apertures on the underside thereof selectively closeable by a leaflet valve if there is any tendency of the blood to flow into the gas dispersion tube. This condition of course, is undesirable since blood flowing into the gas dispersion tube, such as when the gas is shut off, dries and when the gas is turned back on again may be forced into the blood oxygenating chamber in a hemolyzed condition.

In another embodiment of the present invention, a gas dispersion tube is provided having a plurality of rows of apertures with the apertures in each row being of different size. Surrounding the tube is another tube that selectively exposes one of the rows to the oxygenating chamber to vary the gas bubble size injected into the chamber. As discussed above, the smaller the bubble size the greater the difficulty in getting rid of carbon dioxide. Of course, it is desirable to retain some carbon dioxide in the blood by varying the bubble size. Through the selective communication of one row of apertures, the carbon dioxide content may be varied as desired.

The oxygenating chamber is provided at one end of the cubic oxygenator and extends completely across the same. One of the problems in prior art oxygenating devices is that they are not capable of responding to the demands of the patient which may vary from 3 to 7 liters per minute depending upon the size and capacity of the patient as well as on other individual patient variables. To accommodate for these varying flow rates, one wall of the oxygenating chamber is pivotally mounted at its lower end and has a projection extending from the oxygenator housing so that the wall may be pivoted during use to vary the volume of the oxygenating chamber. This not only varies the flow capacity of the oxygenator, but also provides smooth gas dispersion throughout the oxygenating chamber during the gas exchange process.

As the bubbles rise in the vertically oriented oxygenating chamber, there is an increase in bubble size since there is a progressive diminution of the hydrostatic pressure affecting the bubble. As the bubbles increase in size, they develop greater tension or their walls as indicated previously and become more subject to rupture and consolidation into whole blood.

The blood flow rate must be compatible with the metabolic needs of the patient. If the flow rate is less than the maximum capacity of the system, (the oxygenating system), an excess amount of blood will pool in the gas exchange system taxing the total available blood volume of the patient. To eliminate this problem, the movable wall is gradually closed to provide the smooth flow of bubbles upwardly to the top of the oxygenating chamber. This regulates the time interval discussed above that the blood and gas phases are in contact, and hence varies the extent of the gas exchange process. Closing the wall decreases the time of contact and opening the wall increases the time of contact. By regulating the gas input and the volume of the oxygenating chamber, the physician can control the optimum time of exposure, optimum gas partial pressures in the blood, and the efficient utilization of a given volume of blood with minimal churning and also provide optimum bubble size for their ultimate consolidation.

One significant advantage of the present movable wall variable oxygenating chamber is that it may be brought into operation to optimize the processing of the venous blood returned during the actual operation of the system when perfusion of the patient is proceeding.

A generally horizontal bubble collection chamber is provided according to the present invention separate from the oxygenating chamber. The bubble collection chamber is defined by a rigid mesh closed on five sides and open on the sixth to the oxygenating chamber, surrounded by another mesh coated with a suitable defoaming agent and surrounded by a filter. One advantage of this construction and horizontal arrangement of the chamber is that some of the bubbles will pass upwardly into the defoaming mesh above the bubble collection chamber and then after bursting, fall back as whole blood into the collection chamber where is serves as a catalyst for consolidating more bubbles.

The reconstituted whole blood then falls from the defoaming mesh to a slightly inclined ramp that supports the debubbling assembly. From this ramp, blood flows on to still another ramp extending across the oxygenator and defining therein a reservoir. In one embodiment, there is provided a plate spaced from the ramp and disposed in parallel fashion thereto that serves to control the temperature of the blood as it flows in laminar fashion between the ramp and the plate. Moreover, the plate serves as a bubble trap by means of the hydrostatic pressures involved and the laminar flow of the blood between the ramp and the temperature control plate.

In another embodiment, the ramp has a series of corrugations thereon closed on one side to provide for the flow of a temperature controlling fluid therethrough. The corrugations also serve to direct the blood flow in a uniform fashion. The corrugations moreover control the rivulette formation in the blood exiting down the ramp, which prevents the formation of bubbles which would otherwise occur. Another function of the corrugations are to maximize the surface area of the blood exposed to the corrugated ramp which, of course, is subject to temperature control. The corrugated plate may be made of a metaloceramic resistor which will maintain a given temperature evenly throughout the plate when a proper current is applied across it.

In this embodiment, an obturator is provided in the reservoir for the purpose of raising the fluid level in the reservoir and increasing the amount of blood in the reservoir that is in contact with the temperature control surface.

In still another embodiment, temperature control is effected by the provision of a separate mounting member upon which the ramp of the oxygenator rests.

BRIEF DESCRIPTION OF THE DRAWINGS

FIG. 1 is a perspective view of one embodiment of the present invention.

FIG. 2 is a cross-section taken generally along line 2—2 of FIG. 1.

FIG. 3 is a cross-section taken generally along line 3—3 of FIG. 2.

FIG. 4 is a cross-section taken generally along line 4—4 of FIG. 1.

FIG. 5 is a top cross-section taken generally along line 5—5 of FIG. 1.

FIG. 6 is a fragmentary section showing the venous blood and gas dispersion inlets, taken generally along line 6—6 of FIG. 5.

FIG. 7 is a fragmentary section taken generally along line 7—7 of FIG. 2.

FIG. 8 is a fragmentary section of a modified embodiment of the gas dispersion tubing illustrated in FIG. 6.

FIG. 9 is a cross-section of a modified bubble oxygenator according to the present invention with a corrugated reservoir ramp.

FIG. 10 is an enlarged fragmentary section taken generally along line 10—10 of FIG. 9 showing the corrugated ramp.

FIG. 11 is a fragmentary view illustrating a modified gas dispersion tube.

FIG. 12 is a cross-section taken generally along line 12—12 of FIG. 11, and

FIG. 13 is a further embodiment of the present invention.

DETAILED DESCRIPTION OF THE PREFERRED EMBODIMENTS

Referring to the drawings and particularly FIGS. 1–7, an oxygenator 10 is illustrated, which is of the bubble type adapted for cardiopulmonary bypass as well as other bypass procedures. As shown, the oxygenator 10 is generally cubic in configuration and includes a front wall 12, a rear wall 14, and side walls 15 and 16. The back, front and side walls are joined together by a bottom wall 18 and a top wall 20.

Affixed to and projecting from side wall 15 is a gas dispersion inlet fitting 21, a venous return inlet fitting 23, a cardiotomy return inlet fitting 25 and an outlet fitting 28 adapted to receive suitable tubing to return oxygenated blood to the patient.

The gas dispersion fitting 21, the venous return fitting 23 and the cardiotomy return fitting 25 open within the bottom of an oxygenating chamber 27. As shown in FIGS. 2, 6 and 7, the gas dispersion fitting 21 is connected to a gas dispersion tube 30 that extends between the side walls 15 and 16. The gas dispersion tube 30 has two rows of apertures 31 and 32 opening in a generally downwardly direction as shown in FIGS. 6 and 7. Extending over these two rows of apertures 31 and 32 is an arcuate leaflet valve member 34 fixed as at 36 to the central bottom portion of the tube. The leaflet member 34 is flexible and positioned so that when pressure in the oxygenating chamber exceeds the pressure in the gas dispersion tube 31, the leaflet 34, acting as a valve, will close both rows of apertures 31 and 32, preventing the flow of blood into the gas dispersion tube. This prevents the drying of blood within the gas dispersion tube which would result from the flow of blood into the tube upon shutting off the gas supply to the gas dispersion tube, such as when the gas source is changed.

As is known in the art, the gas dispersion fitting 21 is adapted to be connected to a suitable source of respiratory gas such as a 98% oxygen and 2% carbon dioxide mixture.

Mounted immediately above the gas dispersion tube 31 is a venous blood inlet tube 38 which communicates with the venous return fitting 23 and extends between side walls 15 and 16. The tube 38 has a slot opening 40 as shown in FIGS. 6 and 7 which extends a substantial distance between side walls 15 and 16.

The cardiotomy return fitting 25 opens directly into the oxygenating chamber 27 and has no cross tube associated therewith. Cardiotomy return fitting 25 is adapted to be connected to a suitable sucker drawing blood from the patient's wound and generally does not supply a continuous flow of venous blood to the oxygenator 10. Thus blood from the venous return tube 38 is mixed with respiratory gases from the gas dispersion tube 30, with small bubbles being formed, from apertures 31 and 32, of gas within the blood, increasing in size as the fluid pressure decreases as the bubbles move upwardly in the oxygenating chamber 27.

An alternative to the gas dispersion tube 30 is illustrated in FIGS. 11 and 12. In FIGS. 11 and 12, a gas dispersion tube assembly 44 is illustrated that functions basically to selectively vary bubble size of a gas in the oxygenating chamber 27 to vary the carbon dioxide content in the blood as discussed above. Toward this end, the gas dispersion assembly 44 includes an inner pipe 46 having an end 48 adapted to be connected to a suitable source of respiratory gas. The tube 46 has three rows of apertures, 49, 50 and 51 spaced 45° apart. The aperture in one row are of a different size than the apertures in the other rows. Tube 46 is rotatably mounted in an outer tube 53 having an elongated slit 55. With this construction, the inner tube 46 may be rotated by the operator to selectively position one of the rows 49, 50, 51 adjacent slit 55 and in this manner control the bubble size of gas flowing from the tube 46, through slit 55 and into the oxygenating chamber 27.

During change of the gas source, etc., the inner tube 46 may be blocked by rotating the apertureless portion or quadrant 57 coincident slit 55. This prevents any backflow of blood to the gas dispersion tube 46. Moreover, when the slit 55 is blocked by portion 57, a vent 60 outside wall 15' is aligned with a vent in the inner tube 46 permitting the escape of gases outside the oxygenator.

A still further modification of the gas dispersion tubing in the oxygenating chamber is shown in FIG. 8. In the FIG. 8 embodiment, the gas dispersion tube 30' has a plurality of apertures therein and is positioned within an arcuate chamber 60. The chamber is closed by gas dispersion plates 61 and 62 having rows of holes 63 and 64 therein, which are closable by leaflet valves 66 and 67, respectively. Leaflet valves 66 and 67 serve to prevent the flow of blood into the gas dispersion tube 30' by blocking the apertures 63 and 64 upon any tendency of the blood to flow into the chamber 60.

Viewing FIG. 2, the oxygenating chamber of bubble chamber 27 has a variable volume to accommodate varying blood flow rates and to provide for the smooth upward flow and formation of bubbles within the chamber 27. Toward this end, the chamber 27 is defined by a fixed wall 69 having a slight inclination from the vertical and extending between the side walls 15 and 16 as shown in FIG. 3. The other side of the oxygenating chamber 27 is defined by a movable wall 70 pivotally mounted at the juncture of the bottom wall 18 in back wall 14 as at 72. The position of wall 70 is controlled by a projection 73 extending through an aperture 74 and rear wall 14 as shown clearly in FIG. 2. An arcuate member 75 fixed to the top wall 20 seals the upper edge 77 of the movable wall to prevent the flow of blood or blood bubbles around the top and behind the wall 70.

Communicating with the oxygenating chamber 27 through an entrance opening 79 is a debubbling chamber 81 defined by the side walls, top wall 20, liquid blood return ramp 82 and deflecting plate 83. Both the return ramp 82 and the deflecting plate 83 extend between the side walls 15 and 16 as shown in FIG. 3. The blood return ramp has a plurality of parallel ridges 86 as shown in FIG. 3 for supporting a defoaming and filter bag assembly 87. The defoaming bag 87 includes a rigid mesh framework having a top wall 89, front wall 90, bottom wall 91 and a rear wall 92 with the top and bottom walls joined by side walls 95 and 96 as shown in FIG. 3. This interior mesh framework may be constructed of a plurality of 1/16th inch diameter ribs that are fused to produce a diamond shaped space between the ribs of approximately ¼ inch each lengthwise. Interior framework is fused at 97 and 98 to the top plate 20 and the oxygenating chamber plate 69 so that all blood flow from the chamber must pass into the defoaming and filter bag 87. As shown clearly in FIGS. 3 and 5, the interior framework 81 defines a debubbling chamber 100 having a width many times greater than its height, with the chamber 100 being generally horizontally disposed. A plurality of apertures 101 are provided in the bottom 91 of the interior framework 81. The forward propulsion of the respiratory gas and blood input will drive the bubbles through the diamond shaped spaces of the mesh framework.

Surrounding the rigid framework 81 and defining part of the defoaming bag 87 is a loose mesh web 105 defined by layers of a coarse material such as polypropylene net or plastic open pore such as polyurethane, which has been coated with a standard blood defoaming substance such as polymethylsilioxane or a silicone defoaming agent. This mesh is loosely packed in multiple layers. Surrounding the debubbling and defoaming bag 87 is a filter 129. Bubbles from the blood oxygenating chamber 27 enter the chamber 100 and pass into the silicone treated polypropylene mesh 105 and the bubbles are eliminated returning the blood to a fully liquid state. As the bubbles enter the bubble collection chamber 100, portions of the bubbles will pass by gravity downwardly directly into the mesh 105 and the excess gas is eliminated from the blood. Whole blood then collects on the return ramp 82. The spaces between ridges 86 define free flow channels for the return of liquid whole blood.

Other bubbles will pass from the collection chamber 100 in the direction of arrow 110 in FIG. 2 into the mesh 105. These bubbles will contact the mesh 105 eliminating the excess gas with the reconstituted blood falling back into chamber 100 where it acts in a catalytic fashion as a debubbling agent on new bubbles in chamber 100. Excess gas from the main debubbling chamber 81 escapes through a vent 112.

Debubbled whole blood flowing down ramp 82 passes through slit 114 between ramp 82 and diverting plate 83 and flows onto reservoir ramp 115. The ramp 115 extends completely between the side walls 15 and 16 and defines a reservoir 117 for blood in the oxygenator. The ramp 115 has at its end a vertically extending baffle 118 which as shown in FIG. 4 terminates at 119 short of wall 16 to permit blood to flow around the baffle 118 into a trough 120 leading to venous outlet port 28 at the forward bottom of side wall 15. A float 122 is provided in the trough 120 that serves to prevent suction on the outlet 28 from drawing air from the oxygenator reservoir 115 when it is empty of blood. The reservoir 117 has a vent 125 in front wall 12 for the purpose of adding a medicament to the blood when desired. A vent 93 is provided in wall 82 to provide for the free decompression of the reservoir 117.

Spaced closely above the reservoir ramp 115 is a temperature control plate 126 having an upper curved portion 128 for directing blood flow smoothly between the plate 126 and ramp 115. The plate 126 extends for a substantial distance between the side walls 15 and 16. The temperature control plate 126 is either electrically activated, or has suitable water ports for controlling the temperature of the plate 126, and hence the blood flowing between the plate 126 and ramp 115 as well as the blood in reservoir 117. Note also that the sloping character of ramp 115 and temperature control plate 126 serves to increase the exposure of blood in reservoir 117 to the temperature control plate 126.

An additional embodiment of the present invention is shown in FIGS. 9 and 10 wherein an oxygenerator assembly 150 is illustrated. The oxygenator 150 is similar to that described with respect to FIGS. 1–5, except that the blood flow return and reservoir ramps are oppositely disposed and the ramps are of a somewhat different configuration. More specifically, return ramp 151 is forwardly tilted so that blood flow from the debubbling chamber 152 flows through slit port 153 onto combined reservoir ramp and temperature control plate 155. As seen in FIG. 10, the temperature control plate 155 is constructed of a bottom plate 166 and a corrugated top plate 167 having seal points 168. The corrugated top plate 167 defines a series of interconnected channels 170 through which temperature controlled water may flow from port 172 to port 174. The corrugations in plate 155 prevent the formation of bubbles and at the same time assure a smooth, even spread of blood across the surface of ramp 155.

For the purpose of forcing the blood higher in reservior chamber 176, an empty chamber 177 is fixed within the reservoir chamber.

An additional difference in the FIG. 9 embodiment is that movable wall 179 of oxygenating or mixing chamber 180 has its upper end 182 sealed to the deforming bag 82 by flexible plastic member 185, shown at 186.

A further embodiment of the present invention is shown in FIG. 13 wherein an oxygenator 200 is illustrated generally in similar configuration to that shown in FIGS. 1–5. In the FIG. 13 embodiment, however, ramp plate 201 does not serve to control blood temperature, but instead a mounting frame assembly 204 is provided and supports the entire oxygenator housing and has a water channel member 206 congruent with ramp 208 for the purpose of engaging the ramp and controlling the temperature thereof. For the purpose of supplying temperature controlled water to the channel and support 206, inlet fitting 209 and outlet fitting 210 are provided.

I claim:

1. An oxygenator assembly, comprising: housing means, bubble chamber means in said housing means for mixing blood and respiratory gases, reservoir means in said housing means, and means for conveying oxygenated blood from said bubble chamber to said reservior including a generally planar ramp over which blood flows in planar fashion, and means for controlling the temperature of blood flowing over the ramp, a directing plate above said ramp and spaced a small distance therefrom to provide a bubble trap for blood flowing between the ramp and the directing plate, said ramp defining one side of the reservoir within the housing, said reservoir being narrow at the bottom and diverging outwardly in an upward direction.

2. oxygenator assembly, comprising: housing means, bubble chamber means in said housing means for mixing blood and respiratory gases, reservoir means in said housing means, and means for conveying oxygenated blood from said bubble chamber means to said reservoir means including an inclined ramp having an upper face to receive blood from the bubble chamber means and to convey said blood downwardly to the reservoir means, and means for controlling the temperataure of the ramp.

3. An oxygenator assembly according to claim 2, wherein said ramp includes a plurality of corrugations to direct the blood flow downwardly, and the temperature controlling means includes means for closing the lower side of the corrugations, and means for supplying temperature controlling fluid to the closed lower side of the corrugations.

4. An oxygenator assembly according to claim 2, including a directing plate above said ramp and spaced a small distance therefrom to provide a bubble trap for blood flowing between ramp and the directing plate.

5. An oxygenator assembly according to claim 4, in which the means for controlling the temperature of the ramp is provided by temperature regulating means carried by said directing plate.

6. An oxygenator assembly according to claim 4, in which the means for controlling the temperature of the ramp is separate from the housing means and includes a housing support provided with a heat exchange member, said housing means having a recessed portion formed at least partly by the underside of the inclinded ramp and the heat exchange member having an upper portion projecting into said recessed portion adjacent the underside of the inclinded ramp whereby the housing support and its heat exchange chamber will maintain the housing means in upright operative position.

7. A bubble oxygenator device comprising: a housing having a bubble and defoaming chamber and an oxygenated blood reservoir blood chamber formed between sidewalls of the housing; an inlet for respiratory gas to the bubble and defoaming chamber; a venous blood inlet to the bubble and defoaming chamber; and blood outlet from the reservoir chamber; an inclined ramp structure extending between the chambers and having opposite edge portions abutting opposite sidewalls of the housing, said ramp having an upper surface receiving blood from the defoamer and conducting said blood by gravity downwardly to the reservoir chamber; and means for controlling the temperature of said ramp structure to regulate the temperature of the blood passing over said surface.

8. A bubble oxygenator device as specified in claim 7 in which the upper surface of the ramp structure is of troughlike configuration to receive and direct blood to the reservoir chamber.

9. A bubble oxygenator device as specified in claim 7 in which the upper surface of the ramp structure is of corrugated configuration to direct blood to the reservoir chamber and to increase the area of blood contact with the temperature controlling means.

10. A bubble oxygenator device as specified in claim 7 in which the upper surface of the ramp structure is generally planar to receive blood in a broad shallow stream from the defoamer and to direct said stream by gravity to the reservoir chamber.

* * * * *